(12) United States Patent
Fortino

(10) Patent No.: US 6,838,278 B2
(45) Date of Patent: Jan. 4, 2005

(54) DEVICE FOR CELL TRANSFER

(75) Inventor: Terry Fortino, Medford, NJ (US)

(73) Assignee: MidAtlantic Diagnostics, Inc., Marlton, NJ (US)

( * ) Notice: Subject to any disclaimer, the term of this patent is extended or adjusted under 35 U.S.C. 154(b) by 84 days.

(21) Appl. No.: 10/278,216

(22) Filed: Oct. 22, 2002

(65) Prior Publication Data
US 2003/0082798 A1 May 1, 2003

Related U.S. Application Data
(60) Provisional application No. 60/331,079, filed on Oct. 22, 2001.

(51) Int. Cl.[7] .................................. C12M 1/00
(52) U.S. Cl. .............. 435/307.1; 435/309.1; 600/34; 73/864.13; 73/864.16
(58) Field of Search .......... 60/34, 35; 435/307.1, 435/309.1; 73/864.13, 864.16

(56) References Cited

U.S. PATENT DOCUMENTS

| | | | | |
|---|---|---|---|---|
| 5,827,174 A | * | 10/1998 | Reuss et al. ............ | 600/33 |
| 6,027,443 A | * | 2/2000 | Nag ..................... | 600/33 |
| 6,164,280 A | * | 12/2000 | Everett et al. ........... | 128/898 |
| 6,527,703 B2 | * | 3/2003 | Simmet .................. | 600/33 |
| 6,610,005 B1 | * | 8/2003 | Tao ..................... | 600/34 |
| 6,623,422 B2 | * | 9/2003 | Kamrava ................. | 600/34 |
| 2003/0032896 A1 | * | 2/2003 | Bosley et al. ........... | 600/585 |

OTHER PUBLICATIONS

Gibbons et al., "Preimplantation genetic diagnosis for Tay–Sachs disease:successful pregnancy after pre–embryo biopsy and gene amplification by polymerase chain reaction", Fertility and Sterility 1995 63 (4):723–728.

Huang et al., "In Vitro Analysis of Oocyte Cumulus Complex Pickup Rate in the Hamster *Mesocricrtus auratus*", Molecular Reproduction and Development 1997 47:312–322.

* cited by examiner

Primary Examiner—David A. Redding
(74) Attorney, Agent, or Firm—Licata & Tyrrell P.C.

(57) ABSTRACT

A device for transferring cells present in fluid media is provided which is especially useful for in vitro fertilization techniques and intracytoplasmic sperm injection procedures.

8 Claims, 4 Drawing Sheets

DEVICE FOR CELL TRANSFER

INTRODUCTION

This application claims the benefit of U.S. Provisional Application No. 60/331,079, filed Oct. 22, 2001 which is herein incorporated by reference in its entirety.

BACKGROUND OF THE INVENTION

When traditional fertility treatments fail, especially for patients with tubal disease, severe endometriosis, oligospermia and immunologic or unexplained infertility, in vitro fertilization technologies are often helpful. These techniques are, however, complex and require a team of specialists. Ovarian stimulation allows production of multiple oocytes which can then be retrieved by transvaginal ultrasound guided aspiration and handling of the oocytes to outside of the body. The oocytes can then be fertilized in vitro and transferred to the uterine fundus. Skill and specialized devices are required to manipulate and transfer oocytes and embryos during such procedures.

Glass pipettes are traditionally used in surgically assisted reproduction techniques such as in vitro fertilization, to collect and transfer genetic material. For example, glass pipettes are typically used to transfer the cumulus-oocyte-complex from the follicular aspirate to wash and culture media. Similarly, glass pipettes are used to transfer removed blastomere from a multi-celled pre-embryo to a slide or vessel for the purpose of pre-implantation genetic diagnosis (PGD). Gibbons et al. 1995 Fertility and Sterility 63(4):723–8. Huang et al. 1997 Molecular Reproduction and Development 47(3):312–22. However, glass pipettes present major disadvantages in in vitro fertilization techniques including but not limited to, breakage, poor fluid transfer control, scratching of dishes and inflexibility.

The present invention provides a device for manipulation and transfer of cells present in a fluid media. The device is particularly useful in the transfer of cells such as oocytes and blastomeres during in vitro fertilization (IVF) and the transfer of cells for intracytoplasmic sperm injection (ICSI) procedures.

SUMMARY OF THE INVENTION

An object of the present invention is to provide a device for transferring cells present in fluid media. The device comprises a hollow housing having a first open end and a second open end; a plunger sized to fit slidably within the hollow housing; a plunger shaft with a top end and a bottom end, wherein the bottom end is inserted first into the hollow housing and is linearly connected to the plunger at the first open end of the hollow housing to allow movement of the plunger shaft up and down into the hollow cavity of the hollow housing thereby pushing the plunger to extend out of the second open end of the housing; a plunger cap attached to the top end of the plunger shaft sized to cover the first open end of the hollow housing when the plunger shaft is inserted into the hollow housing; a first O-ring positioned adjacent to the second open end of the hollow housing; a hollow spacer positioned adjacent to the first O-ring; a second O-ring positioned adjacent to the spacer so that the first O-ring, the spacer and the second O-ring form a tubular passage through which the plunger moves to enter a pipette tip; a tapered removable collar which is removably attached to the second open end of the hollow housing and which surrounds the first O-ring, the spacer and the second O-ring; and a pipette tip with a first and second open end and an internal diameter sized to transfer cells without damaging the viability of the cells, said pipette tip being secured to the device via the removable collar so that the first end of the pipette tip is adjacent to the second O-ring and the second end of the pipette tip is free to transfer cells.

DETAILED DESCRIPTION OF THE INVENTION

The present invention provides a device for cell transfer which is especially useful for in vitro fertilization (IVF) and intracytoplasmic sperm injection (ICSI) procedures. For example, the device of the present invention can be used to manipulate the cumulus complex and strip cumulus and corona cells from oocytes prior to intracytoplasmic sperm injection procedures. The device of the present invention can also be used to easily remove the corona for assessing the presence of pronuclei in conventional IVF procedures. In addition, the device of the present invention facilitates safe transfer of embryos and oocytes through various selected media and solutions.

Figure 1:
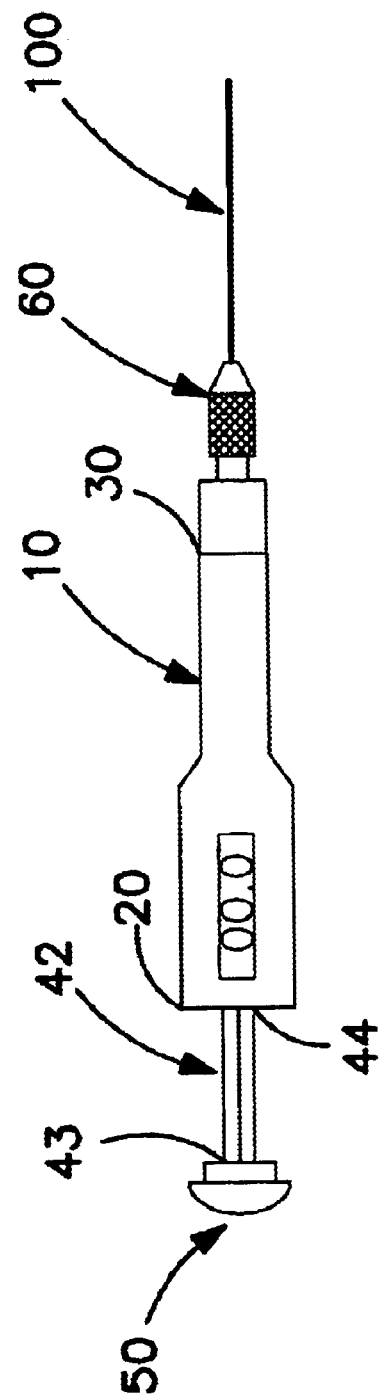
FIG. 1 shows a schematic diagram of one embodiment of the device of the present invention useful for transfer of cumulus complex during in vitro retrieval procedures.

Embodiments of the invention are shown in FIGS. 1 through 4. FIG. 1 shows an embodiment of the invention useful in the transfer of cumulus complex and for softening the cumulus mass in a mild hyaluronidase solution when preparing the oocytes for insemination by intracytoplasmic sperm injection (ICSI) procedures. As shown in FIG. 1, this device comprises a hollow housing 10, a plunger 40, a plunger shaft 42, a plunger cap 50, a first O-ring 80, a spacer 70, a second O-ring 90, removable collar 60, and a pipette tip 100.

The hollow housing 10 of the device has a first open end 20 and a second open end 30. The hollow housing 10 may be either tapered or untapered. The hollow housing may comprise plastic or other suitable materials.

The plunger 40 is sized to fit slidably within the hollow housing 10. It is preferred that the plunger is comprised of stainless steel.

The plunger shaft 42 has a top end 43 and a bottom end 44, wherein the bottom end 44 is inserted first into the hollow housing 10 and is linearly connected to the plunger 40 to allow movement of the plunger 40 up and down inside the hollow cavity of the hollow housing 10. The plunger shaft may further comprise graduations which are representative of the volumetric measurements of the fluids being transferred.

A plunger cap 50 is attached to the plunger shaft 42 which has one end sized to cover the first open end 20 of the hollow housing 10 when the plunger shaft 42 is inserted into the hollow housing 10. The plunger cap may be of any suitable configuration, and may further comprise a finger pad.

A first O-ring 80 is positioned adjacent to the second open end 30 of the hollow housing 10. A hollow spacer 70 is positioned adjacent to the first O-ring 80 with the open centers of the first O-ring and the spacer aligned. A second O-ring 90 is positioned adjacent to the hollow spacer 70 so that the first O-ring 80, the hollow spacer 70 and the second O-ring 90 form a tubular passage through which the plunger 40 moves to enter into a pipette tip 100.

A removable collar 60 is removably attached to the second open end 30 of the hollow housing 10 and surrounds the first O-ring 80, the hollow spacer 70 and the second O-ring 90. It is preferred that the first O-ring 80 has a smaller hole than the second O-ring 90. The first O-ring 80 with the smaller hole is located adjacent to the hollow housing. The spacer 70 is preferably comprised of plastic and has one concave side facing the removable collar. The orientation of the concave side of the spacer toward the hollow housing properly seats the pipette tip 100 and ensures a good seal. The removable collar can be loosened and tightened preferably via rotation of the collar. Accordingly, the removable collar 60 is adjustable and may comprise a threaded lock, interlocking parts or another fastening device which is used to secure the removable collar 60 to the hollow housing 10 in a stationary position. As shown in the cross-sectional view of FIG. 2, the removable collar 60 is attached at the second open end 30 of the hollow housing 10. The removable collar 60 can be formed to taper away from the hollow housing 10. It is preferred that the removable collar 60 has a narrow or tapered end on the side furthest from the hollow housing 10.

The pipette tip 100 has a first and second open end and an internal diameter sized to transfer cells without damaging the viability of the cells. The pipette tip 100 is secured to the device via the removable collar 60 so that the first end of the pipette tip 100 is adjacent to the second O-ring 90 and the second end of the pipette tip 100 is free to transfer cells. In particular, the pipette tip 100 is attached to the device by loosening the removable collar 60 and depressing the plunger cap until the plunger protrudes past the removable collar 60. In a preferred embodiment the plunger 40 protrudes 0.5 to 1.0 cm past the removable collar 60. The pipette tip 100 can be placed over the plunger 40 and pressed firmly along the plunger until it contacts the second O-ring 90 at the tip of the hollow housing 10. The removable collar 60 can then be tightened firmly against the housing.

The pipette tip 100 is preferably unbreakable and both the first end and the second end of the pipette tip 100 are flat. The pipette tip 100 can be packaged in a single sealed container so that the top of the container can be removed while working under a sterile hood. In a preferred embodiment, the pipette tip 100 is sterilized by gamma irradiation. It is further preferred that the pipette tip 100 is mouse embryo tested. It is yet further preferred that the pipette tip 100 is endotoxin tested.

Figure 2:
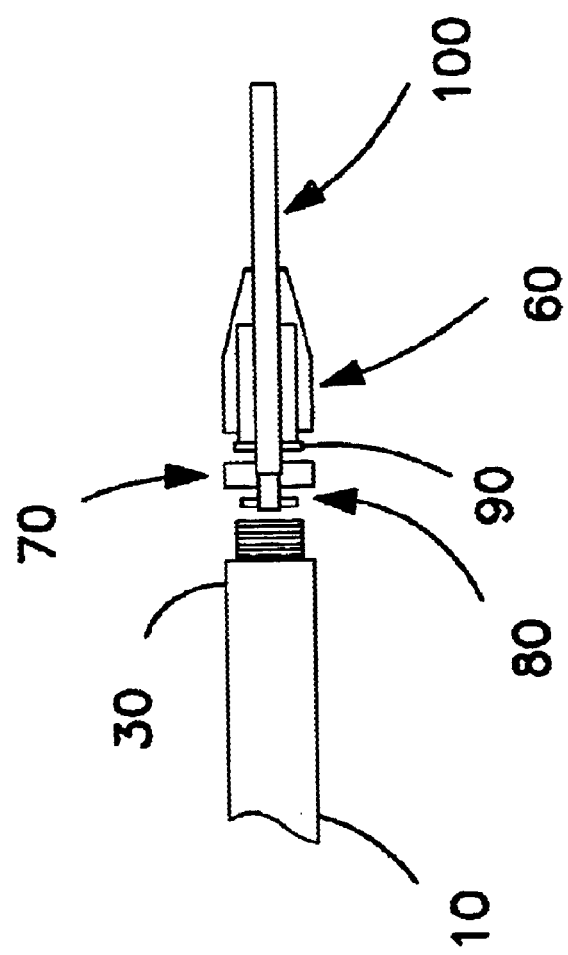
FIG. 2 shows a cross sectional view of the housing, collar and pipette tip of the device depicted in FIG. 1.

In the device embodiment depicted in FIGS. 1 and 2, the internal diameter of the pipette tip 100 is preferably about 1000 microns, so that cumulus-oocyte-complex can be efficiently transferred from follicular aspirate to wash and culture media. The plunger can be set so that the volume of the fluid transferred with the cells is limited. In a preferred embodiment the plunger cap and shaft are depressed so that the plunger protrudes 0.5 to 1.0 cm past the collar. In this manner, the pipette tip 100 does not begin to fill until the plunger, plunger shaft and plunger cap are released.

Figure 3:
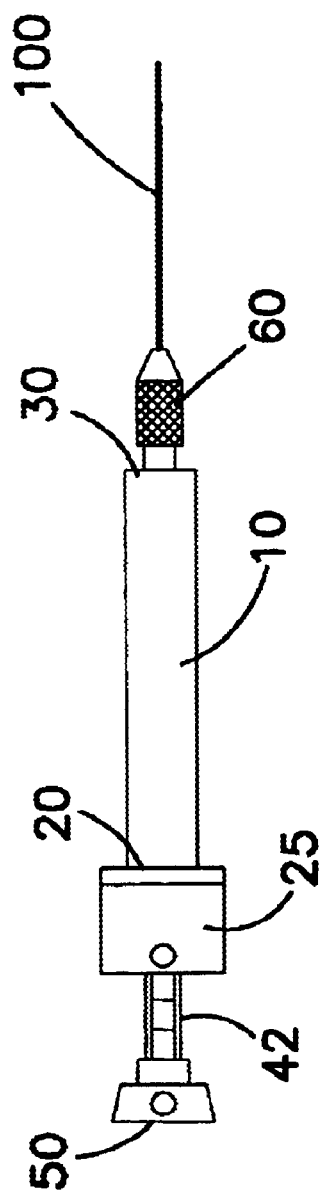
FIG. 3 shows a schematic diagram another embodiment of the device of the present invention useful for the removal and transfer of blastomeres from a multi-celled preembryo.
Figure 4:
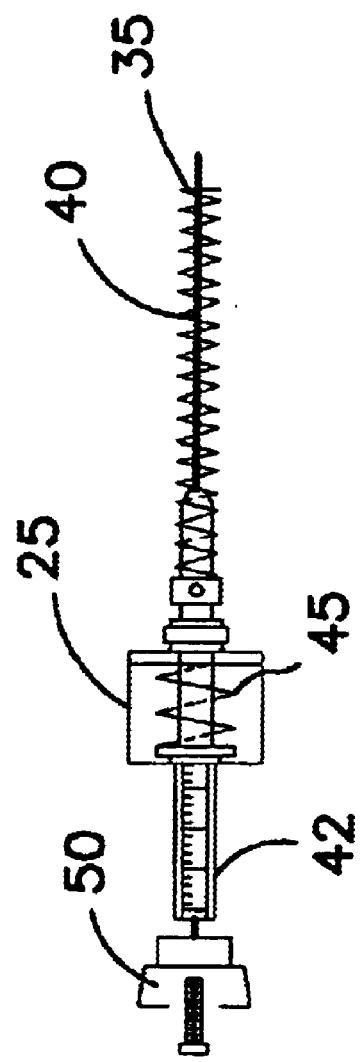
FIG. 4 shows a schematic of a spring assembly used in the device depicted in FIG. 3.

In another embodiment, as depicted in FIGS. 3 and 4, the device of the present invention is designed to transfer a removed blastomere from a multi-celled pre-embryo for Pre-implantation Genetic Diagnosis (PGD) to a reaction vessel or slide. In this embodiment, a spring housing 25 is attached to the first open end 20 of the hollow housing 10. The plunger 40 moves perpendicularly through the open center of the spring housing 25 so that a spring 35 which is wound around the plunger 40 and the plunger shaft 42 is compressed and extended with each perpendicular movement of the plunger 40 and plunger shaft 42. In a preferred embodiment an index control spring 45 is located within the spring hollow housing 25 so that the distance that the plunger is depressed and retracted to attain the desired volume transfer effect is controlled. In this embodiment, the pipette tip 100, preferably has an internal diameter of between about 40 to 60 microns. In a more preferred embodiment, a pipette tip with a 50 micron internal diameter is used. Because of the small internal diameter of the pipette tip 100, the wall of the tip is thicker and the internal diameter is smaller than typical pipette tips. This tip design allows increased flexibility and strength of the pipette tip 100 as compared to typical 50 $\mu$m pipette tips. Also, the smaller internal diameter of the pipette tip 100 allows a thinner plunger to be used in the hollow housing. In a preferred embodiment the pipette tip 100 is flexible. It is further preferred that the tip is comprised of polycarbonate. It is further preferred that the pipette tip 100 is gamma irradiated for sterility. The tips are preferably non-scratching to vessels and plates.

What is claimed is:

1. A device for transferring cells present in fluid media comprising:
   a) a hollow housing having a first open end and a second open end;
   b) a plunger sized to fit slidably within the hollow housing;
   c) a plunger shaft with a top end and a bottom end, wherein the bottom end is linearly connected to the plunger in the hollow housing at the first open end of the hollow housing so that upon compression the plunger extends out of the second open end of the housing;
   d) a plunger cap attached to the top end of the plunger shaft sized to cover the first open end of the hollow housing when the plunger shaft is compressed into the hollow housing;
   e) a first O-ring positioned adjacent to the second open end of the hollow housing;
   f) a hollow spacer positioned adjacent to the first O-ring;
   g) a second O-ring positioned adjacent to the spacer so that the first O-ring, the spacer and the second O-ring form a tubular passage through which the plunger moves to enter a pipette tip;
   h) a tapered removable collar which is removably attached to the second open end of the hollow housing, said removable collar surrounding the first O-ring, the spacer and the second O-ring; and
   i) a pipette tip with a first and second open end and an internal diameter sized to transfer cells without damaging the viability of the cells, said pipette tip being secured via the removable collar so that the first end of the pipette tip is adjacent to the second O-ring and the second end is free to transfer cells.

2. The device of claim 1 wherein the pipette tip has an internal diameter sized to transfer a cumulus-oocyte complex without damage.

3. The device of claim 1 wherein the pipette tip has an internal diameter of about 40–60 $\mu$m.

4. The device of claim 1 wherein the pipette tip has an internal diameter of about 1000 $\mu$m.

5. The device of claim 1 wherein the pipette tip is flat on the open end.

6. The device of claim 1 wherein the pipette tip is disposable.

7. The device of claim 1 wherein the removable collar is adjustable.

8. The device of claim 1 further comprising a spring housing and spring located within the hollow housing and attached to the first open end of the hollow housing, said spring housing and spring controlling compressible and extendable movement of the plunger shaft and plunger.

* * * * *